United States Patent [19]
Cotton et al.

[11] Patent Number: 5,837,552
[45] Date of Patent: *Nov. 17, 1998

[54] SURFACE-ENHANCED ANALYTICAL PROCEDURES AND SUBSTRATES

[75] Inventors: Therese M. Cotton; George Chumanov; Konstantin Sokolov, all of Ames, Iowa; Timothy M. Sheehy, Denville, N.J.

[73] Assignee: Medifor, Ltd., Geneva, Switzerland

[*] Notice: The term of this patent shall not extend beyond the expiration date of Pat. No. 5,527,712.

[21] Appl. No.: 477,288

[22] Filed: Jun. 7, 1995

Related U.S. Application Data

[63] Continuation-in-part of Ser. No. 453,443, May 30, 1995, Pat. No. 5,527,712, which is a continuation of Ser. No. 138,890, Oct. 19, 1993, abandoned, which is a continuation of Ser. No. 858,163, Mar. 27, 1992, abandoned, which is a continuation-in-part of Ser. No. 733,728, Jul. 22, 1991, abandoned.

[51] Int. Cl.⁶ .................................................. G01N 33/553
[52] U.S. Cl. .................. 436/525; 427/2.11; 427/2.13; 427/287; 427/383.1; 427/404; 427/414; 422/57; 422/82.05; 422/82.08; 436/172; 436/518; 436/526; 436/527; 436/531; 436/532; 436/534; 436/805
[58] Field of Search ..................... 427/211, 2.13, 427/287, 383.1, 414, 404; 436/172, 518, 525, 526, 527, 531, 532, 534, 805; 422/57, 82.05, 82.08

[56] References Cited

U.S. PATENT DOCUMENTS

| | | |
|---|---|---|
| 3,926,564 | 12/1975 | Giaever . |
| 3,979,184 | 9/1976 | Giaever .................................... 436/526 |
| 4,090,849 | 5/1978 | Healy et al. ............................. 436/526 |
| 4,267,234 | 5/1981 | Rembaum . |
| 4,267,235 | 5/1981 | Rembaum et al. . |
| 4,369,226 | 1/1983 | Rembaum . |
| 4,438,239 | 3/1984 | Rembaum et al. . |
| 4,978,503 | 12/1990 | Shanks et al. . |
| 4,992,385 | 2/1991 | Godfrey . |
| 5,266,498 | 11/1993 | Tarcha et al. . |
| 5,376,556 | 12/1994 | Tarcha et al. . |
| 5,378,508 | 1/1995 | Castro et al. . |
| 5,527,712 | 6/1996 | Sheehy .................................... 436/525 |

FOREIGN PATENT DOCUMENTS

| | | |
|---|---|---|
| 79200352 | 6/1979 | European Pat. Off. . |
| 85106996 | 6/1985 | European Pat. Off. . |
| 26 38 250 | 8/1976 | Germany . |
| PCT/US90/06013 | 10/1889 | WIPO . |

OTHER PUBLICATIONS

D. A. Weitz, et al., *Journal of Electron Spectroscopy and Printed Phenomena* (Pgs. 363–370), *A Comparison of Raman Scattering, Resonance Raman Scattering, and Fluorescence From Molecules Absorbed on Silver Island Films*, ©1983 Elsevier Scientific Publishing Company.

(List continued on next page.)

*Primary Examiner*—Christopher L. Chin
*Attorney, Agent, or Firm*—Kenneth L. Sherman; Sherman & Sherman

[57] ABSTRACT

Surfaced-enhanced, analytical procedures wherein a surfaced article includes a substrate surface, metal islands, a spacing/coupling agent layer, and binding partner molecules which bond with work piece molecules to be detected. A population of spaced apart metal islands are formed on the substrate and have at least some interconnections formed between them. A continuous layer coats the islands and all surfaces between the islands. The continuous layer includes a coupling agent which immobilizes first binding partner molecules. The first partner molecules bond to the coupling agent and the second binding partner molecules bind to the first binding partner molecules to allow detection of presence or concentration of the work piece binding partner molecules.

35 Claims, 3 Drawing Sheets

OTHER PUBLICATIONS

Cotton, et al., *J. Phys. Chem. 1986*, 90 (Pgs. 6071–6073), *Distance Dependence of Surface–Enhanced Resonance Raman Enhancement In Langmiur–Blodgett Dye Multilayers*, ©1986 American Chemical Society.

Rohr, et al., *Analytical Biochemistry 182* (Pgs. 388–398), *Immunoassay Employing Surface–Enhanced Raman Spectroscopy*, ©1989 Academic Press, Inc.

Freeman, et al., *Science—vol. 267, Mar. 17, 1995* (Pgs. 1629–1632) *Self–Assembled Metal Colloid Monolayers: An Approach to SERS Substrates*.

Grabar, et al., *Analytical Chemistry—vol. 67, No. 4*, Feb. 15, 1995 (Pgs. 735–743), *Preparation and Characterization of Au Colloid Monolayers*, ©1995 American Chemical Society.

SURFACE-ENHANCED ANALYTICAL PROCEDURES AND SUBSTRATES

CROSS REFERENCE TO RELATED APPLICATIONS

This is a continuation-in-part of applicant's presently pending U.S. patent application Ser. No. 08/453,443 filed May 30, 1995, now U.S. Pat. No. 5,527,712, which was a continuation of co-pending application Ser. No. 08/138,890 filed Oct. 19, 1993, now abandoned, which was a continuation of co-pending application Ser. No. 07/858,163 filed Mar. 27, 1992, now abandoned, which was a continuation-in-part of co-pending application Ser. No. 07/733,728 filed Jul. 22, 1991, now abandoned.

FIELD OF THE INVENTION

This invention relates to surface-enhanced chemical analysis procedures or assays, and to consumables used in these procedures.

BACKGROUND OF THE INVENTION

Quantitative analyses of molecular presence and concentrations which are sensitive to extremely low concentrations are regularly made with immunoassay techniques.

The term "immunoassay" is commonly used for analytical techniques in which an antigen and antibody response is measured in order to determine the presence and concentration of either the antigen or antibody. In fact an "immunoassay" is a special case of a more generic technique in which "binding partner molecules" provide a measurable response of the presence or concentration of one of a group of the partners.

In many such situations substances which are neither an antigen nor an antibody provide responses analogous to those of an antigen-antibody system. Each of these "Assays" are partner-specific in the sense that in the correct environment they bind only to their partner molecules. The extent to which this binding occurs is the basis for analytical procedures.

Because immunoassays are the most widely used procedures of this type, they will be described in more detail than the others. However, when the term "immunoassay" is used herein, it is recognized as being descriptive also of surface-enhanced chemical analyses generally, which utilize partner-specific combinations.

As discussed above, the term "immunoassay" is generic to a wide variety of processes and procedures. Basically, it involves a partner specific interaction of a plurality of partner substances which are preferentially attracted to one another.

A well-known example is an antibody of known specificity which is one of the binding partner molecules and is to be receptive to an antigen (the other of the binding partner molecules). The presence and concentration of one of the respective partners is to be detected and measured in the selected immunoassay procedure. As stated above, immunoassays are examples of techniques useful in other than antibody/antigen situations, as will later be discussed.

In immunoassay procedures, the assay depends for its response on the extent to which one "workpiece" binding partner molecule becomes attached to another binding partner molecule. For any assay of this type, a particular partner molecule (often but not always a protein) is attached by some means to a substrate of some kind.

Thereafter, in the course of the assay, the "workpiece" partner molecule which is to be detected and/or measured, contacts the partner on the substrate, sometimes through an intermediate partner molecule. By one means or another, the occurrence and perhaps the extent of the binding reaction between the various binding partner molecules occurs. Then a measurement can be made to determine the presence, and usually also the concentration of the "workpiece" partner.

There are two basic immunoassay analytical techniques, the "sandwich" technique and the "competitive" technique. Both of these techniques are widely used. In each of them, the amount of the partners bonded together is either directly measured, or is measured by way of difference. Persons skilled in this art are already fully aware of these techniques.

It has long been recognized that an immunoassay is a sensitive procedure and is at least theoretically able to perform assays beyond the abilities of even the most sensitive of other known procedures. However, its processes have been very slow and inconvenient to use, sensitivity has been variable and often low, and repeatability has been well below what the process theoretically should be able to deliver. Furthermore, the consumables required for these procedures have had short shelf lives and have required more attention to their use than is desirable in what should be a highly automated and speedy procedure. This is also true of Assays not using antibody/antigen binding situations.

Considerable efforts have been made in the past decade to reduce surface-based analytical processes to a convenient laboratory analysis procedure. Especially strong efforts have been made in surface enhancement.

Some efforts at surface enhancement have produced significant improvements. However these efforts have not provided suitable explanations or understandings of how these improvements occur, or for that matter, even what they are. Instead, the art has developed pragmatically, step-by-step, and by now the dangers of trying definitely to explain the rationale of any new procedures have become very apparent. The newer procedures either work better, or they do not.

As it happens, tremendous increases in sensitivity can be attained with the use of any of the three best-known techniques of surface enhancement. One is surface enhanced fluorescence, another is surface enhanced Raman spectroscopy, and the other is surface enhanced colorimetric procedures. This invention improves the sensitivity, accuracy, convenience, speed and availability of all of these procedures, and provides very effective consumables for use in these procedures.

These procedures for surface enhancement all require the adherence of a specific partner or partners to a surface. Planar, spherical, beads and other non-uniform substrates are known in the art.

One means for enhancing adhesion of a partner to the substrate is to coat the surface of the substrate with a coupling agent which is adherent to the surface.

These procedures are wet processes. The procedures depend on the kinetics of contact between the partner molecule attached to the coupling agent and the patient sample which includes another "workpiece" partner.

The patient sample is characteristically diluted in a buffer solution. As in all contact processes, the gross rate at which the reaction occurs is a function (among other variables) of the total surface area to be contacted, and of the transfer distance the "workpiece" molecules must travel or transfer to reach their partner.

A method for increasing the gross rate is to increase the surface area, and to agitate the reactants to increase the likelihood of access of the "workpiece" partner molecules to the partner on the coupling agent layer. This is a worthwhile approach, but requires a substantial amount of buffer solution. For many procedures this is a viable alternative. However, in many other procedures, the buffered solution includes an expensive partner in wasteful amounts and the cost is extraordinarily high. Such circumstances can exist, for example, when the buffer solution must include as a partner a clonal protein whose cost is very high.

When a large increase in surface area is useful and buffer costs are affordable, a large number of small bodies such as microspheres or beads coated with the coupling agent will advantageously be utilized. Microspheres or other very small bodies coated with a coupling agent will retain many times the amount of partner that would be retained by even a very large number of planar surfaces such as glass slides. This is because of the very large increase in surface area of an increased number of very small bodies, especially of spheres.

A principal advantage of these small substrates is that in a substantial body of liquid they enable the assay process to proceed at rates which approach those defined by solution kinetics. This contrasts with kinetics applicable for reactions at a fixed surface such as glass plate where transfer of molecules is inherently very slow.

The art, as presently known, does not provide a convenient source of a known amount of partner compound for a suitably rapid analysis procedure. All surface-enhanced analytical procedures require a "consumable" which must be provided at the outset of each assay procedure. It is an object of this invention to provide a convenient consumable of known and optimized properties and good shelf life, thereby greatly improving the convenience and reliability of analyses utilizing the partners involved.

In fact, analyses using this invention are more sensitive by at least several degrees of magnitude compared to analogous analytical procedures, and complete their reactions between about 8 and 20 times faster than other known procedures. The repeatability of the procedure is greatly improved, and the analytical procedure can be simplified.

SUMMARY OF THE INVENTION

The present invention provides remarkably improved analytical procedures, and consumables (sometimes called "surfaced articles") for accomplishing them. The present invention provides improved surface-enhanced assay procedures and substrates for use with such improved procedures.

In the present invention the "workpiece" binding partner molecule in the buffering solution is very closely situated relative to the binding partner molecule on coupling layer. The partners are subject to close and uniform capillary forces, so that even without agitation the speed of the reaction approaches that which occurs in a well-stirred solution.

The present invention comprehends the use of substrates which bear metal islands with which a binding partner molecule is physically and spatially related.

The present invention further recognizes that very small metal islands (silver, for example) on a substrate to which a binding partner molecule is directly adherent can result in substantial enhancement of sensitivity of the surface-enhanced analytical process.

A smooth continuous plating of metallic silver does not produce much improvement in sensitivity. However a roughened surface does produce a improvement in sensitivity of assays that is not obtainable with the use of a smooth silver surface, although still much less than that of separate islands.

The reasons for all of this still reside in the realm of speculation, but it is observable that silver islands separate from one another produce a greatly improved assay, and that suitably roughened surfaces give at least some improvement. As will later be disclosed, silver is only one preferred example of a suitable metal for this purpose.

According to a first preferred embodiment of the invention, the substrate is first at least partially surfaced with metal islands. In the first preferred embodiment, these islands are preferably somewhat circular or disc-like, having a very small thickness.

As viewed microscopically, they preferably constitute a discontinuous metal layer. The preferred embodiments of the invention have a substrate which is partially coated or blanketed with very small and very thin metal islands, which may separate from one another. Some of the metal islands are in contact with each other such that metallic interconnections are formed.

A suitable roughened continuous metal surface provides at least some improvement. It appears that the "peaks" of roughness tend to provide structure which at least simulates the properties of isolated metal islands. For this reason, the "peaks" of a suitably roughened metal surface may also be considered "islands," and are within the scope of this invention. In fact, this effect occurs on the surface of suitably rough metal bodies.

In further preferred embodiments, this invention recognizes that metal islands can include small metal particles which are attached to the substrate.

This invention also provides a coupling agent layered between the metal islands and binding partner molecules which additionally serves as a means to accurately space the binding partner molecules from the metal-laden substrate surface. The accuracy of this spacing profoundly increases the sensitivity of the procedure. Further, the coupling layer also protects the partners from deleterious reactions with metals placed on the substrate.

In a first preferred embodiment of the invention polyglutaraldehyde (hereinafter "PGA") is the preferred coupling agent. A suitably prepared surface coated with PGA (or with any other suitable coupling agent) will in fact reliably retain a substantially greater amount of binding molecules partner to its surface than would be retained by a substrate surface which is not coated with such a coupling agent. This is another feature which increases the sensitivity of the procedure.

The enhanced retention of binding partner molecules by the coupling agent along with the accuracy of spacing provided by a carefully controlled thickness of coupling agent constitutes a basis for a multiplied effectiveness of the procedure.

In a second preferred embodiment of the present invention, the coupling agent consists of silica coating layered with a functional coating which may be preferably carboxyl or amino introduced on the surface of the silica layer.

The thickness of this coupling agent layer is established by the parameters of the process to be employed for making it. The coupling agent layer, of any useful thickness will provide for attachment of a larger amount of binding partner molecules than would be bonded to an uncoated surface.

In fact, it is this larger area of effective surface area for partner attachment that in part provides an improved response. The added surface area provides larger amounts of binding partner molecules available to the process and a more uniform concentration of the first binding partner molecules retained on the surfaced article. This further enables a much closer control over the parameters of the process.

The controlled thickness of the coupling agent layer also provides a distance dependent relationship to the degree of enhancement. Surface enhancement is dependent to a surprising degree on the spacing of the binding partner molecules from the metal islands on the substrate.

For fluoroscopic techniques a relatively large spacing provides best enhancement, while for Raman spectroscopy techniques, a smaller spacing provides best enhancement. In both cases there is an optimum spacing, and deviation from it results in less enhancement.

Accordingly, in this invention, the coupling agent has a function in addition to its capacity to bind a partner. The coupling agent additionally provides a very accurate spacing of its exposed surface from the substrate (including the islands) in order to improve the sensitivity of the procedure.

The coupling agent also protects the partner from adverse reaction with the metal.

According to the preferred embodiments of this invention, the area and thickness of the metal islands and the thickness of the coupling agent coating are mutually related relative to the binding partner molecule to be bonded to the coated substrate. The parameters used within the preferred embodiments are chosen to respond most effectively to the radiation or to the response caused by the radiation. The response reflects the presence of, or the concentration of, the "workpiece" binding partner molecules. The physical parameters employed depend on the type of assay (fluorescent, Raman or colorimetric).

In the second preferred embodiment of the present invention, multi-layer substrates are blanketed with a plurality of metal particles and over-coated with a multi-layer coupling agent layer. The coupling agent layer is then blanketed with first binding partners to be used in the chemical analysis as discussed above.

In the preferred embodiment this second embodiment, the substrate may consist of nonreactive silica or latex beads initially coated with a functional layer from the thiol, pyridyl, amino, cyano and carboxyl groups. The substrate is then blanketed with metal particles which may contact each other and form interconnections therebetween.

The metal particles and substrate are then overcoated with a coupling agent layer which may consist of two layers. The initial layer is a non-reactive silica, and a further layer is a functional group of preferably carboxyl or amino introduced on the surface of the silica layer.

The functional layer immobilizes the binding partner molecule on the external surface of the consumable for later immunoassay reactions.

The present invention preferredly uses planar or beaded substrates. However, the present invention further recognizes that other embodiments of the invention may be formed using extended substrate surfaces such as the inside surface of test-tubes, beakers or even coatings upon the outside of fiber optic surfaces. With the present invention, a flat plate can be utilized to provide reaction speeds approaching those of solution kinetics using microspheres with a large reduction in the requirement for a buffering solution. This is accomplished with the use of reaction regions of capillary dimensions.

BRIEF DESCRIPTION OF THE DRAWINGS

The above and other features, organizations, advantages and objects of this invention will be fully understood from the following detailed description and the accompanying drawings. Each of the drawings contained herein are not considered to be accurate depictions of the embodiments of the invention, but are provided for illustrative purposes only and are to be interpreted in conjunction with the attached specification.

DETAILED DESCRIPTION OF THE INVENTION

The following description is provided to enable any person skilled in the art to make and use the invention, and sets forth the best modes presently contemplated by the inventor for carrying out this invention. Various modifications, however, will remain readily apparent to those skilled in these arts, since the generic principals of the present invention have been defined herein.

Figure 1:
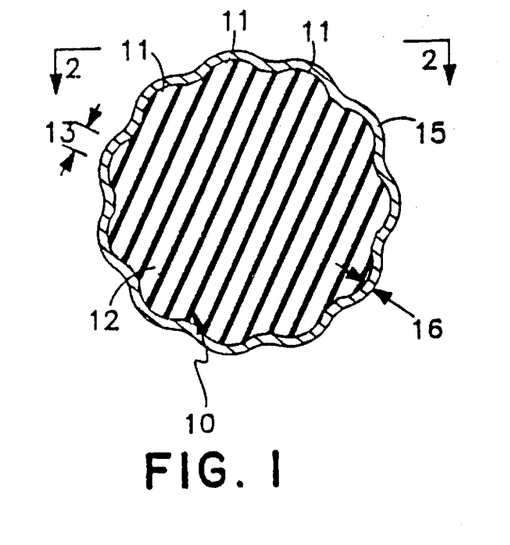
FIG. 1 is a cross section of a first surfaced article according to the first preferred embodiment of this invention.

FIG. 1 shows a first preferred embodiment of one of a plurality of bead substrates for an immunoassay of the present invention. As shown in FIG. 1, a cross-section of a microsphere 10 has a plurality of metallic silver islands 11 on its surface 12. The islands "have a nominal lateral dimension 13 which can conveniently be thought of as the diameter of a circular disk. It is evident that these extremely small islands" will not usually be true circles. Each island "has a nominal thickness 16. The nominal diameter and thickness 16 of the islands" will be discussed later in this specification.

Figure 3:
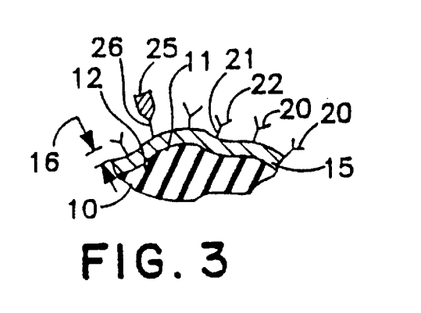
FIG. 3 is a fragmentary portion of FIG. 1, enlarged and utilizing a schematic notation.

FIG. 3 is a schematic diagram intended to illustrate a portion of the surface of a coupling agent 15 coated microsphere 10 which has been contacted by a solution containing a first binding partner molecule 20. Very often this first binding partner molecule 20 will be an antibody.

The first binding partner molecule 20 is bonded or somehow attached to the coupling agent 15. The first binding partner 20 is schematically shown having a stem 21 and a branched receptor 22, which is a conventional schematic representation.

The stem 21 is bonded to the coupling agent 15 and the receptor 22 in actuality has a structure unique to the portion 26 of a second binding partner molecule 25 whose presence and/or concentration are to be detected and measured. The first and second binding partner molecule 20, 25 have a unique relationship to one another through the receptor 22.

The theory of the assay is that a second binding partner 25 has a moiety 26 which "matches" receptor 22, and is captured in it. This simplistic explanation is not rigorous, but it does serve to explain the function of the consumable shown in FIG. 1 which bears the first partner 20.

The first binding partner molecule 20 is selected to be uniquely receptive to a specific second partner molecule 25. When the microspheres 10 are placed in a liquid medium that includes the second binding partner molecules 25 to be detected or measured, the second binding partner molecules 25 seeks out the first partner molecules 20 on the microsphere 10. Thereafter the presence and concentration of the second binding partner molecules 25 can be sensed or measured by known techniques.

As will later be described, in some procedures, the second binding partner molecule 25, which is to be bonded to the first binding partner molecule 20 may not be the substance whose presence or concentration is the subject of the procedure. In some procedures, the "workpiece" molecules (not shown) may not bond directly to the first binding partner molecules 20. This workpiece molecule might be a third binding partner 25 molecule which bonds to the second binding partner molecule 25. The second partners 25 all binding bond to the first partner 20, and the presence and perhaps the amount of the third partner that is bonded in this manner becomes the subject of investigation.

As will later be disclosed, a myriad of the above described, coated beads or microspheres 10 can be used in a liquid suspension to provide a very large reactive surface area as a function of their shape and large numbers. Further, because of their small size, the substrate 10 will tend to remain in suspension without major settling-out for a sufficient and considerable time. This time generally will approach four hours, while the longest procedure will usually require only about one hour. Thus the response of the process using beads microspheres 10 of the preferred embodiment is quite near to that of a true fluid kinetics procedure.

Of course, spheres are not the only useful shape, of a substrate of the preferred embodiment, although they are the most easily made with closely controlled dimensions. Other shapes may also be used bearing in mind the multiplication of total surface area which occurs when a larger body is reduced to a larger number of much smaller bodies. Irregular bodies, or regular bodies of various shapes such as cubes and other polyhedrons can also be used, but are much more difficult to make. All can be suitably coated with metal islands and coupling agent.

Large flat plate substrates have long been used for immunoassays. Plates bearing only silver islands or only coupling agents are known for this purpose, but not in combination to the present knowledge of the inventor herein. The sensitivity of the reaction, in the absence of the combination of islands and a controlled thickness coupling agent as shown by the present invention, is so reduced as to render the process economically non-competitive except in those few instances where there is no viable alternative. The root of the problem is the slow reaction due to the stagnancy of the fluid near the contact surface, and the relatively small total area of the surface, the relatively small amount of partner molecules which will reliably be retained on an uncoated metal surface.

The present invention allows for surface enhancement on a large flat plate substrates. Furthermore, by taking advantage of capillary phenomena, a reaction speed can be attained which approaches that which can be attained with classic fluid kinetics. Furthermore, the volume of expensive buffer solution can be reduced to a bare minimum. In the medical testing field, one test is preferred to another when the costs differ even in fractions of cents and when speeds of tests differ in seconds.

Figure 5:
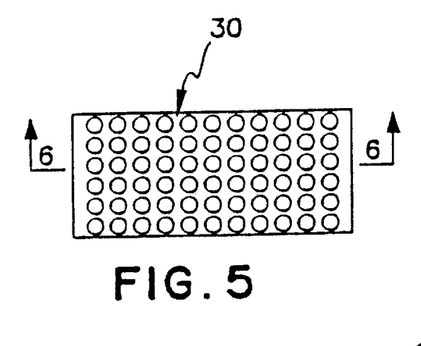
FIG. 5 is a plan view of a second surfaced article according to the first preferred embodiment of the present invention.
Figure 6:
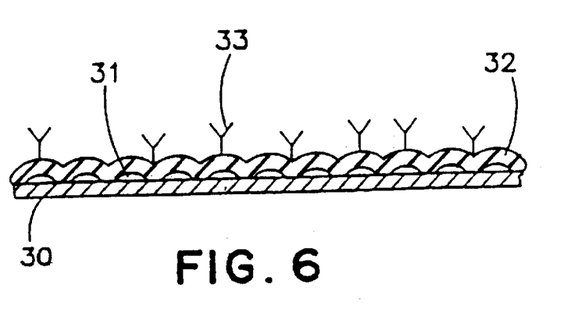
FIG. 6 is a cross-section taken at line 6—6 in FIG. 5.

For this purpose, as shown in FIGS. 5 and 6, a very flat substrate plate 30, usually of glass, has metal islands 31 and a coupling agent layer 32 as previously described for the embodiment shown in FIG. 1. First binding partner molecule 33 is applied to the coupling agent 32, which in this embodiment may be PGA. This surface article and its features are completely identical to that on the microspheres shown in FIG. 1 except for shape.

Figure 7:
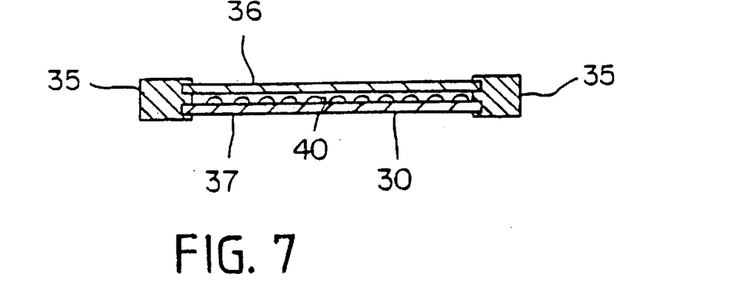
FIG. 7 is a cross-section of a device using the article of FIG. 5 taken at line 7—7 in FIG. 8.
Figure 8:
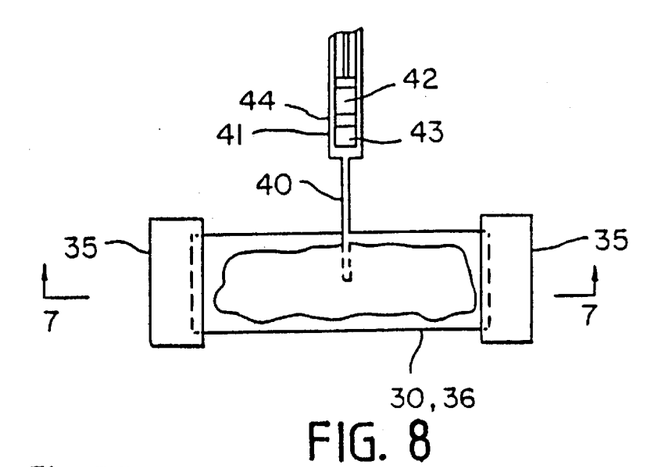
FIG. 8 is a side view of the device of FIG. 7, partly in a cross-section and partly in a schematic notation.

As shown in FIG. 7 and 8, a jig 35 is schematically shown mounting substrate plate 30, and also cover plate 36. Cover plate 36 is supported by the jig 35 parallel to the substrate plate 30, and spaced by a carefully defined spacing 37.

The size of the spacing 37 is determined by the requirement for sufficient buffer solution 42 (including the patient sample 43) to carry out the test, and to assure a capillary action in the fluid between the plates 30, 36. The capillary action assures that the buffer solution 42, 43 will spread to cover the entire exposed surface on the substrate plate 30, and the substances 42, 43 will mix so that no agitation or spreading effort is required.

Furthermore, under these capillary conditions, a thorough mixing of the patient sample 43 and the buffer solution 42 will result, even if they are initially placed between the plates 30, 36 separately.

Even more, the parallelism of the plates 30, 36 and the spreading of the sample-bearing buffer solution 42, 43 results in a thin layer in which transport distance of sample molecules to the coupling agent surface 32 is very short, and the reaction proceeds swiftly. Had the buffer solution 42 and patient sample 43 simply been dropped on an exposed plate, it would have tended to bead up. Too much solution would be required to cover the plate, and the transport distance would have increased, thereby increasing the cost and slowing the test.

A convenient means to introduce the buffer solution 42 and patient sample 43 between the plates 30, 36 is by means of a thin needle 40 moved in a pattern between the plates 30, 36 while discharging the fluids 42, 43 from a syringe 41. The syringe can conveniently be pre-loaded with a known volume 42 of buffer solution and a known volume 43 of patient sample. They may be separated by a "peg" 44 which is a quantity of air to keep them apart in the syringe 41. The volumes 42, 43 will mix thoroughly in the capillary space without agitation. The needle 40 is withdrawn after injection, and can be made a disposable item, as can the syringe 41.

It is convenient for the syringe 41 to be pre-loaded with buffer solution 42 and the peg 35. The syringe 41 can be a stable pre-loaded article, and then the patient sample 43 is drawn into the syringe 41 just before the test.

Manipulation means (not shown) can be provided to move the tip of the needle 40 into the spacing between the plates 30, 36 and to insert and withdraw it.

Figure 9:
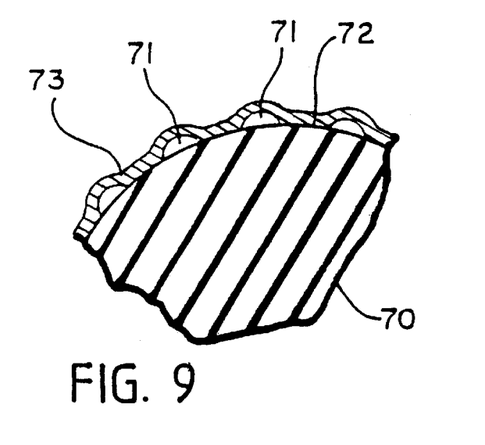
FIG. 9 is a cross-section of a further surfaced article according to the first embodiment of the invention.

FIG. 9 shows a rather unusual further embodiment of the present invention, in which the coupling layer 73 is "imbued" with the first binding partner molecule. FIG. 9 shows a substrate 70 with a silver islands 71 on its surface 72 according to any of the other examples in this specification. In this embodiment, the coupling agent 73 is a layer, laid on the substrate, which is imbued with the first binding partner molecule.

A typical example of coupling agent 73 is a slice of tissue in which a first partner (to be detected) is present within the tissue. Such slices are routinely made by freezing the tissues and slicing it in a microtome while frozen. The tissue is then laid on the substrate 70, where its thickness corresponds with the built-up thickness of the deposited layers described elsewhere herein.

Because of the cellular and permeable nature of tissue 73, the first binding partner molecule will be present on the tissue's exposed surface. In this embodiment, the first binding molecule will behave as though it had been applied as in the other embodiments. Laid layers besides tissue can function in this manner. For example, cellulosic materials, foams and sponges can similarly function in this manner.

All of these embodiments serve to illustrate that the permeability of the coupling agent may be selected based upon the application to which the consumable is to be applied. In the present invention the coupling agent need be retentive to the first binding partner molecule, which may be imbued within the structure of the coupling agent.

Figure 10:
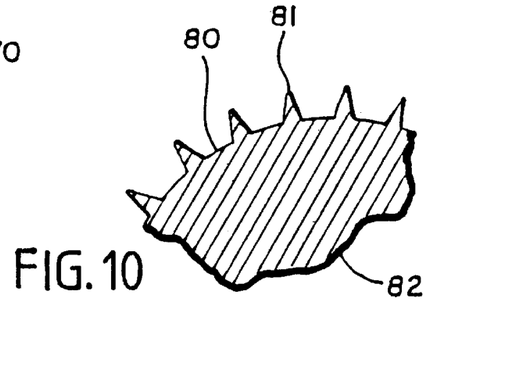
FIG. 10 is a partial cross-section of a further surfaced article according to the first preferred embodiment of the present invention.

FIG. 10 illustrates that a suitably rough surface 80 with islands 81 on a metal body 82 also functions as a consumable within the present invention. The surface of FIG. 10 resembles the surface shown in FIG. 4. However, in the embodiment shown in FIG. 10, the entire substrate is metallic. Colloids and solids have suitably rough surfaces, and a silver colloid suspension with its surface coated with a coupling agent layer will provide improved sensitivity. This is not the preferred embodiment of the invention, but it does provide enhanced sensitivity.

It is an observed fact that different binding partner molecules, for example proteins bonded to a coupling agent and receptive to other partner protein molecules, yield signals of different intensity as a function of thickness of the coupling agent layer, i.e., the binding partner molecule's spacing from the islands. In the embodiments of the present invention, the thickness of the coupling agent layer positions the binding partner molecules at a certain distance to the metal islands so as to enhance the "signals" which are emitted as the consequence of exposure to selected radiation. The sizes and thicknesses of the coupling agent layers and also of the metal islands, are not susceptible to conventional measurement techniques. Instead for commercial production they are best defined by the processes to make them, and by tests which verify their suitability. Such tests can be accomplished by using them in analytical procedures with known concentrations of binding partner molecules.

Consumable small bodies such as beads or microspheres, or larger flat plates, may be defined by the way they are produced. The following description shows the process to produce an effective product which generally will produce several orders of magnitude increase in sensitivity with Raman procedures, and about a four order of magnitude increase with fluorescent and colormetric procedures. Other advantages include speed and greater convenience.

In the first preferred embodiment of the present invention, the substrate may be any suitable non-reactive material to which the metal islands and the coupling-agent can adhere. Polystyrene, glass, latex, polyethylene, nylon, acrylic, polypropylene, silicone rubber, silica and ceramic are all suitable, but not the only substrates possible for use in the embodiments of the present invention.

Polystyrene is the most convenient material for small bodies. Glass is preferred for flat plates. This invention specifically contemplates that other substrates, such as test tube surfaces, beaker surfaces and fiber optic surfaces or any extended substrate surfaces may be used within the invention by applying the principles herein defined.

The cover plate 36 within the embodiments shown in FIGS. 7 and 8 should be made of a material transparent to the radiation used in the analysis and of its response. An acrylic will usually be used.

Nominal diameters between about 0.1 microns and 10.0 microns for the beads or microsphere substrates used in the preferred embodiments have been found to give excellent results. When irregular small body substrates are used, their lateral dimensions will be in this general range.

There are a number of metals which may be used as the islands formed upon the substrate surface. Care will be used in their selection and application.

Useful metals can be selected from the group consisting of silver, copper, gold, platinum, nickel, indium and germanium. Some of these are more effective than others, and some are less suitable for some analyses than others because of their possible adverse effects on the protein. For example, gold, platinum, nickel and copper are antagonistic to some antibodies, but not to proteins which are not antibodies. Copper is generally antagonistic to all proteins.

A suitable coupling agent coating will serve to isolate these metals from the first binding partner molecules and thereby greatly decrease the risk of degradation while still permitting the use of the particular metal island providing for good signal enhancement.

The lesser effectiveness of some of the metals in enhancing the signals strongly supports the use of silver for nearly all procedures. For this reason, silver is used as the illustrative and preferred material in this specification. The process for creating islands of the other metals is similar, differing only in respective process parameters readily known to those skilled in the art.

In the first preferred embodiment of the present invention, the metal islands can be deposited on the substrate surface with the use of any suitable deposition process. Vapor deposition in a vacuum has proved to be the most advantageous. Of course, on beads, microspheres or the like the entire surface may not be coated because part of the surface may be shaded. However, the population of islands will be sufficient and generally consistent so that accuracy of the assay is not adversely affected by the fact that part of the surface does not bear islands.

When isolated islands, separated by substrate surface without metal on it, are to be formed care will be taken to avoid completely plating the surface. In the deposition process, islands will initially form, but as the deposition proceeds and the deposited metal becomes thicker, the islands finally collapse and slump to converge into a continuous plating. This ultimate result can be avoided by careful control over the deposition process, and by stopping it immediately when the islands are sufficiently formed. Experience with the process, and adjustment of the timing and conditions of deposition will soon enable the operator to prepare suitable island-coated substrates.

The most effective silver islands have a nominal height (thickness) between about 20 angstroms and about 200 angstroms. On a bead or microsphere, optimum silver islands will have the following dimensional relationship:

Metal Thickness Nominal diameter+Metal Thickness= between about 0.58 and about 0.67

Substrate bodies bearing a layer of small metal islands are next coated with a coupling agent. The ultimately desired thickness of the coupling agent layer for many assays is between 1 Angstrom and about 100 nm, depending on the analytical technique being used, i.e., fluorescent, Raman, or colorimetric.

In the first preferred embodiment a suitable short term coupling agent may be selected from the group consisting of polyglutaraldehyde (PGA), protein A, protein G, polystyrenes, polyethylenes, polyacrylamides, streptavidin, avidin, and in some procedures, slices of tissue or of other porous material of suitable thickness as shown in FIG. 9. All of these will suitably adhere to the exposed surface of the substrate body between the islands, and to the islands themselves. They form a surface with a spacing from the islands and form a barrier which isolates the metal islands from the first binding partner molecule. In addition, and very importantly, the partner will bond to them.

While it has been found that PGA is extremely suitable as a coupling agent layer for short term effectiveness of the consumable, it has additionally been determined that long-term signal degradation occurs with any permeability of the coupling agent layer. Therefore, PGA is used as a preferred coupling agent layer in the first preferred embodiment of the invention for illustrative purposes.

As discussed below, with respect to the second preferred embodiment of the present invention, long term coupling agent layers are constructed from multiple layers. A first layer is impermeable material, and a second layer is a layer to immobilize the first binding partner molecule on the consumable's surface. These are the two general purposes of the coupling agent layer. First to impermeably space the binding partner molecules from the metal islands. Second to immobilize the binding partner molecules for their combination with their partners.

PGA is by far the most effective short-term coupling agent and the easiest with which to form a layer to a controllable thickness. The other substances may be deposits formed by well-known techniques. The tissue slice will be laid on the surface, but because of its nature, its respective underlying substrate will be a flat plate rather than a microsphere.

PGA is a condensation product from glutaraldehyde. Initial purity of at least 90% monomer is desirable. Before adding the microspheres, an aqueous solution of glutaraldehyde, about 1.5–4.0% is buffered to between about pH 8.0 to pH 11.8, and maintained at a temperature between about 22 degrees C. and 37 degrees C. for between about 30 to 90 minutes. If the pH is lowered, the time will be increased within these limits, and vice versa. It is not intended that polymerization proceed too far in this solution. Instead, it is intended for the layer to "grow" on the substrate such as the beads or microspheres shown in FIG. 1.

After sufficient time has elapsed, the microspheres will be added to the solution although if preferred, the microspheres may be added to the aqueous glutaraldehyde earlier. The solution must be maintained on the basic side. pH 10.0 is usually a minimum number pH.

The microspheres will be left in the solution for between about 3 to 48 hours, with stirring as necessary to avoid clumping. If the microspheres were added earlier, the elapsed time will be shorter. By this time, a suitable layer of PGA will have been deposited. Later measurements and comparison with the parameters which produced them will, with little experimentation, find the optimum conditions for making the intended product.

Next the solution is poured off of the microspheres, which are then washed with a buffered phosphate solution at pH between about 4.0 and 8.0. This will rinse off the unbound PGA. Several rinses will be needed, each to be poured off. The product will not be dried.

The cleansed microspheres are suspended in an assay buffer, and the first binding partner molecules respective to an intended future test are added. The first binding partner molecule will attach itself to the PGA layer. The entire PGA layer will receive the partner, and retain it stably in quantities greater than the uncoated substrate would have retained it. The binding partner molecule located over the metal islands will provide an enhanced signal, as will later be discussed.

After leaving the beads/microspheres in the partner-containing solution for a sufficient period of time at the proper pH and temperature, the solution will be decanted and the microspheres will be washed several times with a solution of the assay buffer.

If desired, the microspheres can now be treated with a blocking agent. The purpose of the blocking agent is to bind to all unoccupied sites on the PGA surface, that is, sites not already occupied by the first binding partner molecules. A generally useful blocking agent is BSA (bovine serum albumen) in aqueous solution.

This is the "consumable" sent to the user for use in assays which utilize the first binding partner molecule carried by the microspheres. Of course a different binding partner molecule will be provided for assaying different substances, but each is respective to some intended assay.

Consumables using other shapes are formed with the same procedures. Small bodies of sizes comparable to the beads on microspheres are treated just as described above.

Flat plates pr extended surfaces will receive metal islands as described above, on one side. The coupling agent layer may thereafter be provided upon the entire plate in the solution as described. A masking may be provided on one side if it is desired to coat only one side with the coupling agent layer, or by any other suitable means to isolate and treat only one side of the plate.

If "islands" are to be formed as part of a continuous metal layer that totally covers a substrate, it is necessary to roughen the layer to create them. For example, in FIG. 4, metal islands 85 are shown rising above a metal coating 86 which envelopes a plastic substrate body 87, perhaps spherical as in FIGS. 1, 2 and 3.

Figure 2:
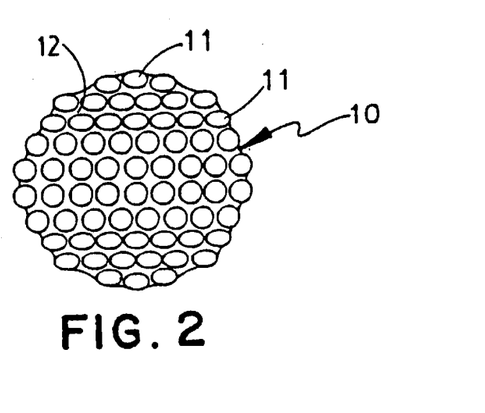
FIG. 2 is a side view taken at line 2—2 in FIG. 1.

This embodiment will not function as effectively as islands which are more specifically formed as in FIGS. 1–3, but they will still function to improve sensitivity.

Figure 4:
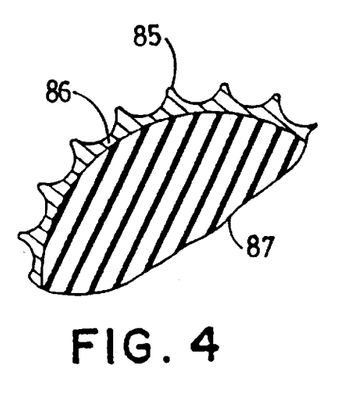
FIG. 4 is a fragment similar to FIG. 1 showing a different arrangement of metal islands.

To create the embodiment shown in FIG. 4, a continuous, uniform metal plating can be first applied to the substrate. Then by ion erosion or otherwise, the metal surface is pitted or otherwise eroded so that some "peaks" of metal rise between "valleys" on the surface. It appears that at least some enhancement is attained with these peaks, and the term "islands" as used herein refers both to those shapes which are spaced apart by metal plating and those which are spaced apart by unplatted substrate material.

For the embodiment of FIG. 10, the treatment is the same as when a non-metal substrate is used except that colloidal particles are generally suitably rough when formed, and often will not require subsequent treatment.

Flat plates and discrete particles in suspension have been described as examples of suitable supports (substrates) for the consumable. However, the coupling agent can be applied to other useful types of extended surfaces or supports, for example to the inside of test tubes, to beads in a column, to the wall of a column, to the surface of a foldable bag, to micro-titer plates, strips, and wells, as examples. In these examples, coated particles can be applied to the surfaces, or these various surfaces can be provided with metal islands and then coated with coupling layers. There is no limit to the range of applications.

The procedures for use of the first binding partner molecule in assay procedures are conventional and known, and require no detailed description here. Briefly stated, the coated substrate whether small bodies, on a plate bearing the first partner or other extended surface, will have applied to it a know quantity (sample) of test serum containing the second binding partner molecule (occasionally also a third binding partner molecule) being assayed in a suitable buffer solution. The presence or absence, and if present the concentration of this second or third binding partner molecule is determined by a subsequent procedure.

In addition there will be added a known amount of the same second or third binding partner molecule for which the assay is intended. However, this additional second or third binding partner molecule is "marked" (the sample partner is not marked). For fluoroscopic assays, it is dyed with a fluorescent dye. This is the arrangement for "competitive" type assays. For Raman-type assays, the additional second binding partner molecule is supplied with a Raman tag.

In both cases, the sample second binding partner molecules and added second binding partner molecules tend to bond to the first binding partner molecules on the substrate.

After a suitable period of incubation, generally between about 5 and about 180 minutes, the consumable will be exposed to appropriate radiation and the emissions will be measured.

In the fluoroscopic assay, the bound material fluoresces more vigorously than the unbound. Alternately, the consumable can be bleached out, and it can be observed that the bound material continues to respond. In either event, the fluorescence is significantly increased by the presence and correct dimensions of the metal islands and of the coupling agent layer.

With Raman-type assays, the emissions from the bound material are more vigorous than of the unbound material because of the precise spacing of the metal from the Raman tag. This appears to yield a much stronger signal. In selecting the thickness of the coupling agent layer it will be noted that Raman type assays best utilize thinner layers, and fluorescent and colorimetric type assays tend to use thicker layers.

The following are lists of binding partners which can be utilized in pairs, or in some analyses, three partners. Speaking generally partner A will usually be the partner supplied on the consumable, while partner B and/or C will generally (but not always) be the subject of the analysis, and will be applied to the consumable during the analytical procedure.

PARTNER A
   any antibody
   any hapten
   any derivatized hapten
   any nucleic acid antigen
   any lipid
   any polysaccharide
   any nucleotide
   any protein antigen
   protein A
   protein G
   any cellular antigen in tissue
   any aromatic
   or organic compound PARTNER B
   specific binding partners to any
   of partners A, further including but not
   limited to
   an organic derivative
   a biotinylated antibody
   streptavidin
   avidin
   and any of the above labelled
   with a Raman tag, or with a fluorescent
   or colorimetric dye PARTNER C
   specific binding partners to
   any of partners B labelled with
   a Raman tag or with a fluorescent
   or colorimetric dye, the partner B
   not being labelled.

It will be observed that many of the binding partner molecules can be used as first, second or third binding partner molecules. Their characterization is not intended to reduce the scope of their utility. Instead, the term first binding partner molecule is used to denote the binding partner molecule which will be applied to, or be imbued within, the coupling agent layer. The second binding partner molecule is the binding partner molecule added during the analytical procedure, usually as a sample and as a marked or tagged moiety as well. Partner C denotes the binding partner molecule which couples with the second binding partner molecule, to be sensed or measured after the second binding partner molecule have coupled with the first binding partner molecules.

Examples of well-known suitable first binding partner molecules are rabbit IgG, goat IgG, and mouse IgG, and can be monoclonal in nature. These are antibodies which normally exhibit high specificity and good kinetic binding characteristics.

Examples of well-known second and third binding partner molecules are antigens that can be assayed with the consumable of this invention are:
lipopolysaccharides; proteins such as viral proteins, human proteins and tumor markers; complex carbohydrates such as glucagon and insulin; and aromatic hydrocarbons such as are found in air pollutants.

Stated generally, the foregoing lists, which are not exclusive of other analogous substances, represent a broad range of utility which will serve laboratories well. They provide consumables in which measurable and known quantities of binding partner molecules with which other binding partner molecules can be used to carry out an analysis. In summary it is emphasized that this invention does not reside in any particular immunoassay technique.

By the use of the combination of a substrate with metal island on it and a coupling agent on it of known thickness, and a first partner on the surface of the coupling agent, then an analytical procedure can be made which is remarkably faster and more sensitive than known procedures.

This invention thereby provides a consumable having a surface which bears a binding partner molecule useful in analytical procedures. The sensitivity of the process is greatly increased by virtue of the small metal islands, and the spacing of the partner from the metal island by a layer of coupling agent.

Figure 11:
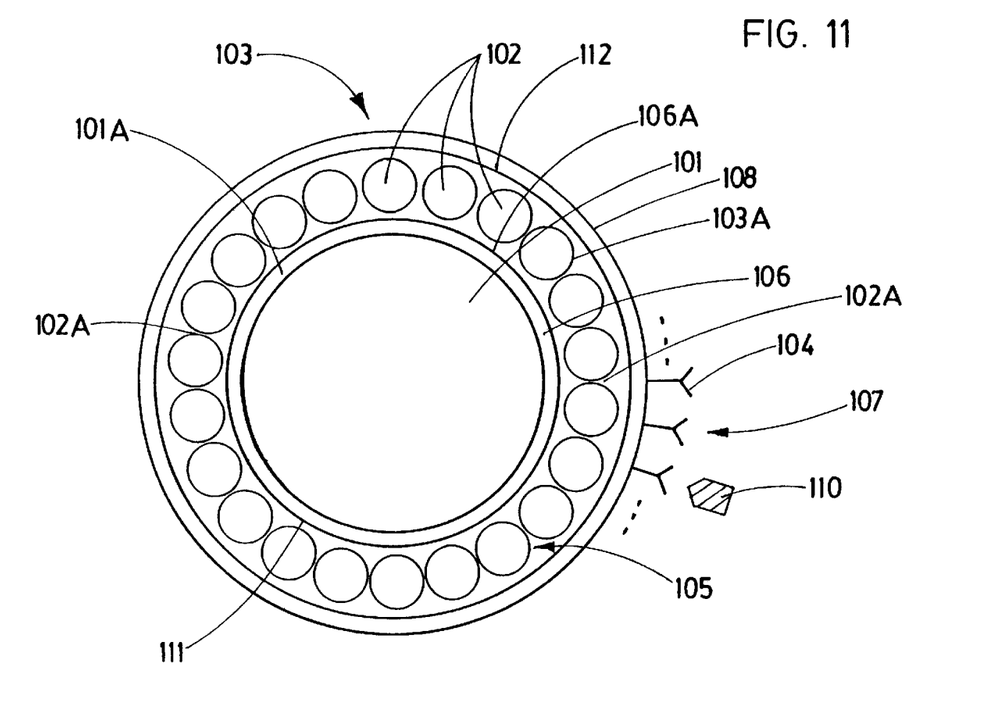
FIG. 11 is a cross section of a first surfaced article according to a second preferred embodiment of the present invention.

FIG. 11 shows a second preferred embodiment of one of a plurality of bead substrates for an immunoassay of the present invention. As shown in FIG. 11, in the second preferred embodiment of the present invention, bead substrates 111 are blanketed with a plurality of metal particles 102 and over-coated with a coupling agent layer 103. The coupling agent layer 103 is then blanketed with first binding partners 104 to be used in the chemical analysis as discussed above.

In the second preferred embodiment of the present invention, non-reactive beads 101 preferredly consist of silica or latex beads. The size of the beads 101 are approximately 0.1–1.5 micrometers and are commonly and commercially available from Bangs Laboratories Incorporated, 979 Keystone Way, Carmel Ind. 46032-2823.

In the second preferred embodiment of the present invention, prior to combination with the metal particles 102, the surface 101A of the non-reactive beads 101 is first coated with a functional coating 106 that has the capability to form strong covalent bonds with the metal particles 102. This functional coating 106 is approximately several molecular layers thick.

Depending upon the beads 101 and the metal particles 102 that may be chosen, the preferred functional coating 106 may be preferably chosen from the thiol, pyridyl, amino, cyano and carboxyl groups.

In this second preferred embodiment of the invention, the non-reactive beads 101 are preferably silica. The surface 101A of the silica beads 101 is modified by commonly known silanization reactions. The following compounds are used in the silanization reaction: trichloro-, trimethoxy- and triethoxy-silanes containing a fourth substitute with a terminal functional group (as listed above).

The silanization reaction is performed under reflux conditions for 10 minutes in a solution containing the silanization reagent (0.02–2%) in alcoholic solutions (e.g. propanol or ethanol) containing a controlled amount of water (2%) or no additional water.

Acidic hydrolysis (hydrochloric acid is added to pH 2–5.5) of the silanization reagent at room temperature may also be used as a method for surface modification. The reaction time is 10–15 minutes. The water content is 0.02–2% and the silane concentration is 0.02–2%.

Following completion of the silanization reaction, the modified beads are centrifuged (5000 g), washed repeatedly with the solvent used in the reaction and water and finally dried under vacuum (0.01 psi) at 100° C. for 10–15 minutes.

All reagents are commercially available, for example from Gelest Incorporated, 612 William Leigh Drive, Tullytown, Pa. 19007-6308.

Latex beads 101 may also be used as a non-reactive bead substrate 101. Latex beads 101 already coated 106 with carboxyl, amino, hydroxyl and pyridyl functional groups are commercially available from Bangs Laboratories, 979 Keystone Way, Carmel Ind. 46032-2823. To introduce other functional groups, the silanization reactions described above for silica beads may be performed on the latex beads coated with the surface hydroxyl groups.

Beads 111 are then blanketed with metal particles 102. The metal particles 102 are attached to the external surface 106A of the beads 111. At some places around the circumference of the external surface of the beads 111, the metal particles 102 contact each other to form metal interconnections 102A.

The metal particles 102 are preferably silver or gold, but as discussed above, can be selected from the group consisting of silver, copper, gold, platinum, nickel, indium and germanium. The metal particles 102 range in size between approximately 100 Å to 1500 Å.

The metal particles 102 are preferably prepared in a colloidal solution by the chemical reduction of metal salts by reducing agents or laser ablation. Examples of suitable reducing agents are sodium citrate, sodium borohydride or sucrose. These methods of preparations are described extensively in the literature and are incorporated herein by preference. For example, J. Neddersen, G. Chumanov, and T. M. Cotton Appl. Spectrosc, 47, 1959 (1993), J. A. Creighton, C. G. Blatchford, M. G., Albrecht, J. Chem, Soc. Faraday Trans. II, 75, 790 (1979). D. C. Lee and D. Meisel J. Phys. Chem. 86, 3391 (1982). G. Fens Nature, Physical Sciences 241, 20 (1973), R. M. Wilenzick, D. C. Russell, R. H. Marriss, S. W. Marshall J. Chem. Phys. 47, 553 (1967).

The preferred method for silver colloid production is to prepare a solution of 0.18 mg/mL of silver nitrate in water, heat the solution to 100° C. and add 0.02% (w/w) sodium citrate to the solution. The solution is kept at the boiling point for 1–2 hours.

The combined 105 metal particles 102 and beads 111 are prepared by incubating the colloidal metal suspension with the beads 111 for periods ranging from one hour to several weeks. The colloid concentration is varied between an optical density of 0–0.1–20 (preferred is 3–10) and the particles between 0.1–3% (w/w).

Beads 111 with the attached metal particles 102 are next over-coated with a protecting coupling agent layer/spacer 103 of controlled thickness. The thickness of this coupling agent layer 103 varies between approximately 30 Å to 1000 Å.

This coupling agent layer 103 serves at least two (2) purposes. Initially, the coupling agent layer 103 protects the metal particles 102 from possible etching by high concentrations of salts (normal saline).

Additionally, the coupling agent layer 103 provides spacing or distance between the chemical reaction occurring between the binding partner molecules 104, 110 external 107 to the coupling agent layer 103 to achieve and allow for a maximum fluorescence enhancement. It is believed that the thickness of the coupling agent layer 103 compromises the enhancement quenching properties of the metal particles 102.

In the second preferred embodiment of the invention, the coupling agent layer 103 includes two layers. Initially, a silica coating or layer 103A is coated upon the combined 105 metal particles 102 and beads 111. A silanization reaction is again used to produce the silica layer 103A surrounding and attached metal particles 102.

The protocol of the silanization reaction is similar to that described above, except tetra-chloro-, tetramethoxy-, or teraetthoxy silanes are used as the reagent in this step. The thickness of the layer is controlled via varying the concentration of the saline reagent and the reaction time.

In the silanization reaction tetraethoxy- or tetramethoxysilane is used in alcoholic solution. Ammonia (0.501M) is used as the catalyst and the water concentration is 3.032M. If tetracholorsilane is used no catalyst or water is added. The reaction time is 15 hours and the temperature is 40° C.

For 0.4 micrometer particles, the preferred solvent is isopropanol. Ammonia and water concentrations are as above. The particle concentration is 0.014% (w/w) and the triethoxysilane is 0.5 mM. This produces a 100 Å spacer layer.

After the desired thickness of the silica layer 103A is built, the layered beads 112 are then centrifuged, washed repeatedly with the solvent used in the reaction and water and finally dried under vacuum at ca. 100° C. for several hours. The preferred thickness 50–100 Å. The centrifuge parameter is 5000 g. The solvent is alcoholic (isopropanol) and preferred drying time is 15 hours.

The second layer 103B of the coupling agent layer 103 consists of a second functional coating 103B which immobilizes the first binding partner molecule 104 on the outside of the coupling agent layer 103. The second functional coating 103B is approximately several molecular layers thick.

The second functional coating 103B may be preferably carboxyl or amino introduced on the surface of the silica layer 103A via the silanization reaction described earlier.

The silanization reaction is performed under reflux conditions for 10 minutes in a solution containing the silanization reagent (0.02–2%) in alcoholic solutions (e.g. propanol or ethanol) containing a controlled amount of water (2%) or no additional water.

Acidic hydrolysis (hydrochloric acid is added to pH 2–5.5) of the silanization reagent at room temperature may also be used as a method for surface modification. The reaction time is 10–15 minutes. The water content is 0.02–2% and the saline concentration is 0.02–2%.

Following completion of the silanization reaction, the modified beads are centrifuged (5000 g), washed repeatedly with the solvent used in the reaction and water and finally dried under vacuum (0.01 psi) at 100° C. for 10–15 minutes.

Immobilization of the first binding partner molecule 104 on the outside of the coupling agent layer 103 is performed using standard protocols described in the literature (e.g., protocols in Pierce Handbook/Catalogue).

The preferred protocol consists of the following steps. A suspension of 0.1% of silica beads 101, containing metal particles 102 and the coupling layer 103 dissolved in MES (4-morphilnoethansulfonic acid) buffer (50 mM, pH 5.5). Add 5 mg/mL EDC (1-ethyl 3-(3-dimethylaminopropyl) carbodiimide hydrochloride) and immediately after the first binding partner (104) up to final concentration (60–100 microgram per mL). Incubate for 15–20 minutes at room temperature. Wash one time in MES buffer. Resuspend in 0.1 MPBS buffer, pH 7.2, containing bovine serum albumin (BSA), 5 mg/mL. Allow the suspension to stand overnight at 4° C. Before the reaction with the second partner 110 the particles with the first partner molecules 104 should be washed one time in PBS buffer pH 7.2.

Figure 12:
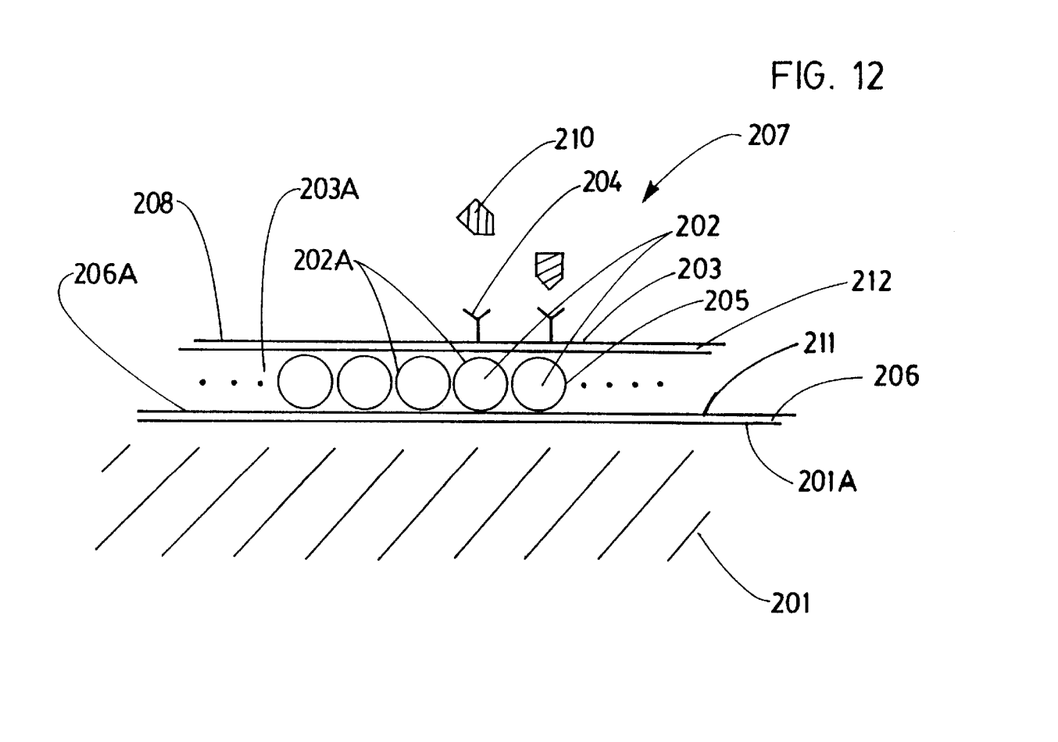
FIG. 12 is a cross section of a second surfaced article according to a second preferred embodiment of the present invention.

FIG. 12 shows a further embodiment of the second preferred embodiment of the present invention shown in FIG. 11. FIG. 12 shows an embodiment of the invention layered upon a flat substrate 211. The flat substrate 211 is layered with metal particles 202 and then covered with a coupling agent layer 203. The coupling agent layer 203 is then blanketed with first binding partners 204 to be used in the chemical analysis as discussed above.

In the second preferred embodiment of the present invention, non-reactive flat substrate 201 preferredly consists of silica or latex.

In the embodiment of the present invention shown in FIG. 12, prior to combination with the metal particles 202, the surface 201A of the non-reactive substrate 201 is first coated with a functional coating 206 that has the capability to form strong covalent bonds with the metal particles 202. This functional coating 206 is approximately several molecular layers thick.

Depending upon the substrate 201 and the metal particles 202 that may be chosen, the preferred functional coating 206 may be preferably chosen from the thiol, pyridyl, amino, cyano and carboxyl groups. The surface 201A of the substrate 201 is modified by commonly known silanization reactions. The following compounds are used in the silanization reaction: trichloro-, trimethoxy- and triethoxy-silanes containing a fourth substitute with a terminal functional group (as listed above). The silanization reactions used for the embodiment of FIG. 12 are similar to the reactions used for the embodiment used in FIG. 11.

Substrate 211 is then blanketed with metal particles 202. The metal particles 202 are attached to the external surface 206A of the substrate 211. At some places along the surface of the substrate 211, the metal particles 202 contact each other to form metal interconnections 202A.

The metal particles 202 are preferably silver or gold, but as discussed above, can be selected from the group consisting of silver, copper, gold, platinum, nickel, indium and germanium. The metal particles 202 range in size between approximately 100 Å to 1500 Å. The metal particles 202 are prepared in the same manner as discussed above for the embodiment shown in FIG. 11.

The substrate 211 with the attached metal particles 202 are next over-coated with a protecting coupling agent layer/spacer 203 of controlled thickness. The thickness of this coupling agent layer 203 varies between approximately 30 Å to 1000 Å.

This coupling agent layer 203 serves at least two (2) purposes. Initially, the coupling agent layer 203 protects the metal particles 202 from possible etching by high concentrations of salts (normal saline).

Additionally, the coupling agent layer 203 provides spacing or distance between the chemical reaction occurring between the binding partner molecules 204, 210 external 207 to the coupling agent layer 203 to achieve and allow for a maximum fluorescence enhancement. It is believed that the thickness of the coupling agent layer 203 compromises the enhancement quenching properties of the metal particles 202.

In the embodiment of the invention shown in FIG. 12, the coupling agent layer 203 includes two layers. Initially, a silica coating or layer 203A is coated upon the combined 205 metal particles 202 and beads 211. The protocol of the silanization reaction to produce the silica layer 203A surrounding the bead 211 and attached metal particles 202 uses tetra-chloro-, tetramethoxy-, or teraetthoxy silanes as the reagent as described above for the embodiment shown in FIG. 11 The thickness of the layer is controlled via varying the concentration of the saline reagent and the reaction time.

After the desired thickness of the silica layer 203A is built, the layered substrate 212 is then washed repeatedly with the solvent used in the reaction and water and finally dried under vacuum at ca. 100° C. for several hours.

The second layer 203B of the coupling agent layer 203 consists of a second functional coating 203B which immobilizes the first binding partner molecule 204 on the outside of the coupling agent layer 203. The second functional coating 203B is approximately one molecular layer thick.

The second functional coating 203B may be preferably carboxyl or amino introduced on the surface of the silica layer 203A via the silanization reaction described earlier.

Immobilization of the first binding partner molecule 204 on the outside of the coupling agent layer 203 is performed using standard protocols described in the literature as discussed above with respect to the embodiment shown in FIG. 11. (E.g., protocols in Pierce Handbook/Catalogue.)

Those skilled in the art will appreciate that various adaptations and modifications of the just described preferred embodiments can be used and configured without departing from the scope and spirit of the invention. Therefore, it is to be understood that, within the scope of the appended claims, the invention may be practiced other than as specifically described herein.

What is claimed is:

1. A surfaced article for use in surfaced-enhanced, analytical procedures, comprising:

a substrate body having a substrate surface;

a population of spaced apart metal islands on said substrate surface;

interconnections being formed between at least some of the metal islands, the interconnections being metal and of lesser thickness than the metal islands;

a continuous layer coating said islands, and also coating all surfaces between the metal islands which were exposed before the continuous layer was applied, said continuous layer including a coupling agent; and first and second binding partner molecules, the first partner molecules bonded to the coupling agent and the second binding partner molecules not bonded to the coupling agent, the first binding partner molecules being binding partners of the second binding partner molecules, said first and second partner molecules being different molecules having specific binding affinity for each other, and said second binding partner molecules binding to said first binding partner molecules.

2. A surfaced article for use in surfaced-enhanced, analytical procedures, comprising:

a roughened metallic layer having top surfaces;

a continuous layer coating the top surfaces of the roughened metallic layer which top surfaces were exposed before the continuous layer was applied, said continuous layer including a coupling agent; and first binding partner molecules bonded to the coupling agent;

second binding partner molecules not bonded to the coupling agent; and wherein the first binding partner molecules are binding partners of the second binding partner molecules, said first and second partner molecules being different molecules having specific binding affinity for each other, and said second binding partner molecules binding to said first binding partner molecules.

3. The surfaced article of claim 2, further comprising a substrate body having a substrate surface supporting the metallic layer.

4. The surfaced article of claim 3, wherein the substrate body is nonreactive.

5. The surfaced article of claim 3, further comprising a functional coating layered between the substrate surface and the metallic layer the functional coating being a material capable of forming strong covalent bonds with metal.

6. The surfaced article of claim 3, wherein the substrate surface is an extended surface.

7. The surfaced article of claim 5, wherein the functional coating is chosen from thiol, pyridyl, amino, cyano and carboxyl groups.

8. The surfaced article of claim 3, wherein the substrate body is planar.

9. The surfaced article of claim 3, wherein the substrate body is a bead.

10. The surfaced article of claim 9, wherein there are a plurality of surfaced articles wherein each substrate for each surfaced article is one of a plurality of beads in solution.

11. The surfaced article of claim 3, wherein the roughened metallic layer includes a population of spaced apart metal islands on said substrate surface.

12. The surfaced article of claim 11, wherein the metal islands are circular or disc-like.

13. The surfaced article of claim 11, wherein the metal islands are small metal particles.

14. The surfaced article of claim 11, further comprising interconnections being formed between at least some of the metal islands, the interconnections being metal and of lesser thickness than the metal islands.

15. The surfaced article of claim 11, wherein at least some of the metal islands are separate from one another, and at least some of the metal islands contact one another forming the metallic interconnections.

16. The surfaced article of claim 11, wherein the metallic layer is a roughened silver layer.

17. The surfaced article of claim 16, wherein the coupling agent coats all surfaces between the metal islands.

18. The surfaced article of claim 2, wherein a metallic particle having a roughened external surface is the roughened metallic layer supporting the continuous layer.

19. The surfaced article of claim 2, wherein the coupling agent separates the metallic layer and the binding partner molecules and provides a predetermined distance between the metallic layer and the binding partner molecules.

20. The surfaced article of claim 2, wherein the coupling agent is polyglutaraldehyde (PGA).

21. The surfaced article of claim 2, wherein the coupling agent layer includes a silica coating layered with a functional coating.

22. The surfaced article of claim 21, wherein the functional coating is chosen from carboxyl, hydroxyl, thiol, pyridyl or amino.

23. A surface-enhanced analytical process, which comprises:

providing a roughened metallic layer having top surfaces;

coating the top surfaces of the metallic layer with a coupling agent;

attaching a first binding partner molecule to the coupling agent;

adding a second binding partner molecule in proximity to the first binding partner such that the second binding partner will bind with the first binding partner;

providing a radiated signal from a source to determine the presence or concentration of the second binding partner molecule.

24. The process of claim 23, further comprising the step of selecting a substrate to support the metallic layer.

25. The process of claim 24, further comprising the step of modifying the substrate surface with a silanization reaction.

26. The process of claim 23, further comprising the step of layering a functional layer between the substrate and the metallic layer the functional layer being a material capable of forming strong covalent bonds with metal.

27. The process of claim 23, wherein the step of providing a roughened metallic layer further comprises blanketing the surface of the substrate with metallic particles.

28. The process of claim 27, further comprising the step of allowing the metal particles to touch to form metal interconnections.

29. The process of claim 27, further comprising the step of preparing the metal particles in a colloidal solution by chemical reduction of metal salts by reducing agents or laser ablation.

30. The process of claim 29, wherein the metal particles are between about 100 Å and about 1500 Å.

31. The process of claim 23, wherein the step of providing a roughened metallic layer further comprises depositing metal islands on a substrate such that the metal islands partially cover the substrate by timing the deposition process to stop when the islands are formed between 20 and 200 angstroms.

32. The process of claim 23, wherein the step of providing a roughened metallic layer further comprises forming the roughened metal layer by first depositing metal upon a substrate and then eroding the metal.

33. The process of claim 23, further comprising the step of determining the thickness of the coupling agent layer.

34. The process of claim 23, wherein the step of forming the coupling agent layer further includes the steps of forming a silica coating above the metallic layer, causing a silanization reaction upon the silica coating and then forming a functional layer upon the modified silica coating.

35. The process of claim 23, wherein the functional coating is chosen from carboxyl, hydroxyl, thiol, pyridyl or amino.

* * * * *